United States Patent

Riecke et al.

Patent Number: 5,411,856
Date of Patent: May 2, 1995

[54] CARBAMYL-SUBSTITUTED BIS(VINYLSULFONYL) METHANE HARDENERS

[75] Inventors: Edgar E. Riecke, Pittsford; Kenneth G. Harbison, Rochester, both of N.Y.

[73] Assignee: Eastman Kodak Company, Rochester, N.Y.

[21] Appl. No.: 179,471

[22] Filed: Jan. 10, 1994

[51] Int. Cl.$^6$ .................................. G03C 1/30
[52] U.S. Cl. ...................... 430/622; 430/621; 430/631; 530/354; 252/182.17; 106/125; 564/204
[58] Field of Search ............ 430/622, 621, 631; 530/354; 252/182.17; 106/125; 564/204

[56] References Cited

U.S. PATENT DOCUMENTS

| | | | |
|---|---|---|---|
| 3,232,764 | 2/1966 | Allen et al. | 430/420 |
| 3,642,486 | 2/1972 | Burness et al. | 430/543 |
| 3,841,872 | 10/1974 | Burness et al. | 430/415 |
| 3,951,940 | 4/1976 | Ballantine et al. | 430/623 |
| 4,063,952 | 12/1977 | Himmelmann et al. | 430/422 |
| 4,088,495 | 5/1978 | Habu et al. | 430/623 |
| 4,104,302 | 8/1978 | Smith et al. | 103/60 |
| 4,137,082 | 1/1979 | Sera et al. | 430/622 |
| 4,142,897 | 3/1979 | Habu et al. | 430/624 |
| 4,173,481 | 11/1979 | Sera et al. | 430/621 |
| 4,323,646 | 4/1982 | Bergthaller et al. | 430/622 |
| 4,338,394 | 7/1982 | Himmelmann et al. | 430/621 |
| 4,349,624 | 9/1982 | Sobel et al. | 430/622 |
| 4,476,218 | 10/1984 | Ogawa et al. | 430/539 |
| 4,554,247 | 11/1985 | Yamashita et al. | 430/622 |
| 4,618,573 | 10/1986 | Okamura et al. | 430/558 |
| 4,673,632 | 6/1987 | Okamura et al. | 430/621 |
| 4,845,024 | 7/1989 | Himmelmann et al. | 430/622 |
| 4,863,841 | 9/1989 | Okamura et al. | 430/621 |
| 4,877,724 | 10/1989 | Chen et al. | 430/621 |
| 4,894,324 | 1/1990 | Himmelmann et al. | 430/622 |
| 4,897,344 | 1/1990 | Okamura et al. | 430/138 |
| 4,939,079 | 7/1990 | Wolff et al. | 430/558 |
| 5,017,463 | 5/1991 | Inoue et al. | 430/398 |
| 5,057,407 | 10/1991 | Okamura et al. | 430/531 |
| 5,071,736 | 12/1991 | Ikenoue et al. | 430/622 |
| 5,236,822 | 8/1993 | Riecke et al. | 430/621 |

FOREIGN PATENT DOCUMENTS

| | | | |
|---|---|---|---|
| 61-018942 | 7/1984 | Japan . | |
| 1018942 | 7/1984 | Japan | 1/30 |
| 1018942 | 1/1986 | Japan | 430/621 |
| 3009343 | 6/1989 | Japan | 5/13 |
| 0207247 | 8/1990 | Japan | 430/622 |
| 5011395 | 1/1991 | Japan | 1/30 |
| 5053236 | 8/1991 | Japan | 1/30 |
| 5011396 | 1/1993 | Japan | 1/30 |
| 1397905 | 6/1975 | United Kingdom | 430/622 |

Primary Examiner—Thomas R. Neville
Attorney, Agent, or Firm—Alfred P. Lorenzo

[57] ABSTRACT

Novel compounds represented by formula (I)

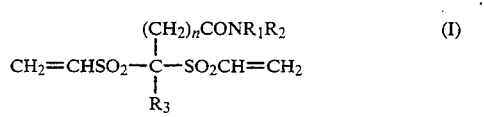

wherein $R_1$ and $R_2$ represent hydrogen or alkyl, $R_3$ represents hydrogen, alkyl, substituted alkyl or $CONR_1R_2$, and n is 0 to 6, can be used to harden gelatin. The compounds are particularly useful for hardening gelatin of a photographic element.

4 Claims, No Drawings

CARBAMYL-SUBSTITUTED BIS(VINYLSULFONYL) METHANE HARDENERS

FIELD OF THE INVENTION

This invention relates to a hardening method for gelatin by an improved hardening agent, and to gelatin so hardened. In particular, this invention relates to a hardening method for gelatin which is used in a silver halide photographic element, and to the resulting photographic element. The invention also relates to novel compounds useful as hardeners for gelatin.

BACKGROUND OF THE INVENTION

Gelatin is commonly used as a binder in photographic light-sensitive materials. Typically, light-sensitive silver halide layers, filter layers, interlayers, antihalation layers, overcoat layers, and backing layers contain gelatin as the main binder.

Photographic materials are generally processed in aqueous processing solutions at various temperatures and pH values. If the photographic material contains gelatin that has not been treated with a crosslinking agent (hardener), such processing results in excessive swelling and poor mechanical strength, which can cause uncontrolled image development and physical damage, respectively. And if the processing solution is maintained at a typical elevated temperature, e.g., 40° C., the gelatin binder can dissolve, causing the layers of the photographic material to disintegrate.

In these photographic materials, gelatin can be hardened with various known compounds to reduce swell, and provide good mechanical strength, and resistance to melting of the layers that contain hardened gelatin. Of the many possible hardeners that are available, the hardeners most frequently used by one or more manufacturers of silver halide photographic materials are aldehydes, active halogen compounds, activated olefins and carboxyl-activating compounds.

These commonly used hardeners, however, have one or more disadvantages, when used in photographic light-sensitive materials. These disadvantages include (1) insufficient hardening, (2) slow hardening during storage (afterhardening), (3) low aqueous solubility, (4) adverse effect on photographic characteristics, such as fog and sensitivity (speed), (5) loss of hardener efficiency caused by interaction with other photographic additives, such as couplers, (6) adverse photographic effects caused by interaction with other photographic additives, such as couplers, and the like.

Aldehydes, especially formaldehyde, are well known, commonly used, and relatively inexpensive hardeners. Typical examples of aldehyde hardeners are described in U.S. Pat. No. 3,232,764. Several problems are encountered when aldehyde hardeners are used. Severe health hazards are a concern with the use of aldehydes as hardeners which causes significant handling difficulties. This is a particularly significant problem for formaldehyde because of its volatility. Also, because of its volatility, it is difficult to control the application level of formaldehyde, which can result in significant hardness variability. Another problem is that significant afterhardening occurs with the use of formaldehyde. Still another problem is that aldehydes can react with couplers, which reduces the effectiveness of both the hardener and the coupler.

Problems associated with volatility can be solved by the use of certain well known and commonly used active halogen hardeners, such as described in U.S. Pat. No. 3,951,940. Frequently used active halogen hardeners include 1,3-dichloro-5-hydroxy-S-triazine (DCHT) and 1-chloro-3,5-dihydroxy-S-triazine (CDHT) and derivatives thereof and mucochloric acid. Although active halogen hardeners are usually not volatile, several other problems can be encountered when they are used. One problem is that significant afterhardening frequently occurs. Another problem is that these hardeners release chloride ion during the hardening process, which can cause deleterious sensitometric effects. Another problem is that these hardeners are easily destroyed by hydrolysis, which makes them difficult to prepare, store, and use.

Problems associated with volatility and afterhardening can be solved by the use of certain carboxyl-activating hardeners, such as formamidinium compounds as described in U.S. Pat. No. 4,673,632, heterocyclic dications as described in U.S. Pat. No. 5,236,822, and carbamoylpyridinium compounds as described in U.S. Pat. No. 4,063,952. However, several problems are encountered when these hardeners are used. One problem is that by-products can adversely affect the physical (e.g., tackiness) and sensitometric (e.g., speed and fog) properties of the photographic elements in which they are used. Also, these by-products are sometimes volatile, foul smelling compounds, which can cause health and odor problems. These problems are often aggravated by the fact that carboxyl-activating hardeners are relatively inefficient so that a relatively large amount of hardener is often required to achieve the desired hardening effect. Carboxyl-activating hardeners undergo rapid hydrolysis and they frequently are hygroscopic. These two properties combine to make these hardeners difficult to prepare, store, and use. Still another problem is that carboxyl-activating hardeners can react with couplers, which reduces the effectiveness of both the hardener and the coupler. One attempted solution to this problem was to use carboxyl-activating hardeners only in combination with 2-equivalent couplers, as described in U.S. Pat. Nos. 4,618,573 and 4,863,841. Another attempted solution to this problem was to limit the carboxyl-activating hardener to only certain zwitterionic dication ethers as described in U.S. Pat. No. 4,877,724. However, these potential solutions severely limit the choice of coupler or hardener and do not eliminate the other problems associated with carboxyl-activating hardeners.

Problems associated with by-products and poor hydrolytic stability can be solved by the use of certain activated olefin hardeners such as described in U.S. Pat. Nos. 3,642,486 and 3,841,872. Also, activated olefin hardeners are usually more efficient than hardeners of other classes. However, several problems are frequently encountered when activated olefins are used as hardeners. One problem is that they frequently cause afterhardening. These problems are particularly severe when certain acryloyl compounds, such as 1,3,5-tris(acryloyl)hexahydro-S-triazine, certain vinylsulfonylacetamido compounds as described in U.S. Pat. No. 4,137,082, or certain heterocyclic vinylsulfones as described in U.S. Pat. No. 4,840,890 are used. One attempted solution to the solubility problem was to use a tertiary amine adduct of a heterocyclic vinylsulfone hardener (as a vinylsulfone precursor) as described in U.S. Pat. No. 4,845,024. However, this results in a tertiary amine by-product that can cause deleterious physical and sensitometric effect. Another attempted solution to the solubility problem was to use a sulfoxyethylsulfone hardener (as a vinylsulfone precursor) as described in U.S. Pat. Nos. 4,338,394 and 4,894,324. However, this results in a release of sulfuric acid, which can cause deleterious sensitometric effects. Another attempted solution to the solubility problem was to use a hardener derived from the reaction of a compound having at least three vinylsulfonyl groups and a compound having at least one group (e.g., carboxyl or sulfo) to increase aqueous solubility and at least one group capable of reacting with the vinylsulfonyl group as described in U.S. Pat. Nos. 4,142,897 and 4,554,247. Other attempted solutions to the solubility problem were to use certain vinylsulfone hardeners that have a sulfophenyl group as described in U.S. Pat. No. 4,897,344, certain vinylsulfonylacetyl compounds as described in JP 5,011,395, certain vinylsulfonylmethylsulfones as described in JP 5,011,396, or certain N,N'-bis(vinylsulfonylmethyl)ureas or N,N'-bis(vinylsulfonylmethyl) thioureas as described in JP 5,053,236. However, these compounds are difficult to prepare and purify and they cause relatively severe afterhardening.

It is therefore desirable to provide a hardener that effectively hardens gelatin, is easily and safely synthesized, purified, and handled, is highly water soluble, causes little afterhardening, and does not cause significant deleterious physical and sensitometric effects. It is toward that end that the present invention is directed.

In the photographic arts, there is an abiding interest in providing new classes of hardener compounds such as provided herein. In view of this interest and in view of the hardening properties of the compounds of this invention, it is believed that this invention represents a substantial contribution to the art.

The hardeners of the present invention are characterized by their rapid hardening effects, high aqueous solubility, high aqueous stability, lack of hygroscopicity, lack of deleterious by-products, and/or a lack of deleterious interaction with other photographically useful substances.

SUMMARY OF THE INVENTION

An object of this invention is to provide a gelatin hardener that exhibits a rapid hardening effect on gelatin so as not to cause prolonged afterhardening.

Another object of this invention is to provide a gelatin hardener that does not release by-products upon reaction with gelatin.

Another object of this invention is to provide a gelatin hardener that is soluble in aqueous media.

Another object of this invention is to provide a gelatin hardener that is not hygroscopic nor susceptible to hydrolysis.

Yet another object of this invention is to provide a photographic light-sensitive material containing a novel gelatin hardener having the above-noted properties.

As a result of extensive investigations, it has now been found that the above objects can be accomplished by hardening gelatin using a novel gelatin hardener represented by the formula (I):

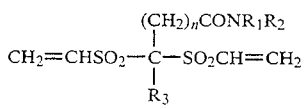 (I)

wherein $R_1$ and $R_2$ represent hydrogen or alkyl, $R_3$ represents hydrogen, alkyl, substituted alkyl or $CONR_1R_2$, and n is 0 to 6.

One aspect of this invention comprises a compound having the formula (I):

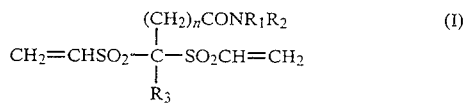 (I)

wherein $R_1$ and $R_2$ represent hydrogen or alkyl, $R_3$ represents hydrogen, alkyl, substituted alkyl or $CONR_1R_2$, and n is 0 to 6.

Another aspect of this invention comprises a method of hardening gelatin which comprises reacting gelatin with a compound represented by formula (I):

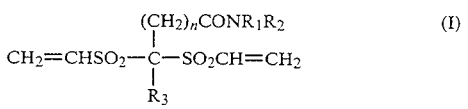 (I)

wherein $R_1$ and $R_2$ represent hydrogen or alkyl, $R_3$ represents hydrogen, alkyl, substituted alkyl or $CONR_1R_2$, and n is 0 to 6.

Another aspect of the invention comprises gelatin hardened with a compound having formula (I):

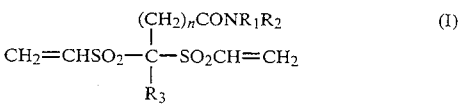 (I)

wherein $R_1$ and $R_2$ represent hydrogen or alkyl, $R_3$ represents hydrogen, alkyl, substituted alkyl or $CONR_1R_2$, and n is 0 to 6.

A further aspect of this invention comprises a method of making a photographic element which comprises coating onto a support at least one layer containing gelatin and a compound of formula (I):

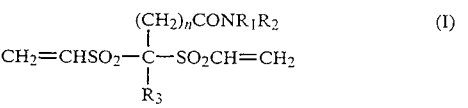 (I)

wherein $R_1$ and $R_2$ represent hydrogen or alkyl, $R_3$ represents hydrogen, alkyl, substituted alkyl or $CONR_1R_2$, and n is 0 to 6; and then permitting the gelatin to harden.

Yet another aspect of this invention comprises a photographic element comprising at least one layer containing gelatin hardened with a compound of formula (I):

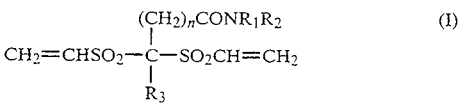 (I)

wherein $R_1$ and $R_2$ represent hydrogen or alkyl, $R_3$ represents hydrogen, alkyl, substituted alkyl or $CONR_1R_2$, and n is 0 to 6.

Advantageous Effect of the Invention

Generally the compounds of this invention harden gelatin relatively quickly and without the release of by-products. Certain of the compounds of this invention are particularly advantageous for use in hardening gelatin in a photographic coating composition having a relatively low pH, e.g. pH of 5. The compounds are easily handled; they are not hygroscopic nor susceptible to hydrolysis. Further, the compounds are soluble in water and certain of the compounds exhibit superior water solubility.

DETAILED DESCRIPTION OF THE INVENTION

The novel gelatin hardener of this invention comprises a compound represented by formula (I):

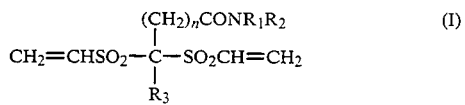

wherein $R_1$ and $R_2$ represent hydrogen or alkyl, $R_3$ represents hydrogen, alkyl, substituted alkyl or $CONR_1R_2$, and n is 0 to 6.

Suitable alkyl groups preferably contain 1 to 6 carbon atoms, and may be straight chain or branched. Substituted alkyl groups preferably contain a solubilizing substituent, such as a carboxyl group.

Specific, but non-limiting examples of compounds represented by formula (I) in accordance with the present invention are shown below in Table 1.

TABLE 1

| | |
|---|---|
| $\begin{array}{c} CONH_2 \\ \| \\ CH_2=CHSO_2-CH-SO_2CH=CH_2 \end{array}$ | Compound H-1 |
| $\begin{array}{c} CONHCH_3 \\ \| \\ CH_2=CHSO_2-CH-SO_2CH=CH_2 \end{array}$ | Compound H-2 |
| $\begin{array}{c} CON(CH_3)_2 \\ \| \\ CH_2=CHSO_2-CH-SO_2CH=CH_2 \end{array}$ | Compound H-3 |
| $\begin{array}{c} CH_2CONH_2 \\ \| \\ CH_2=CHSO_2-CH-SO_2CH=CH_2 \end{array}$ | Compound H-4 |
| $\begin{array}{c} CH_2CONHCH_3 \\ \| \\ CH_2=CHSO_2-CH-SO_2CH=CH_2 \end{array}$ | Compound H-5 |
| $\begin{array}{c} CH_2CON(CH_3)_2 \\ \| \\ CH_2=CHSO_2-CH-SO_2CH=CH_2 \end{array}$ | Compound H-6 |
| $\begin{array}{c} CONH_2 \\ \| \\ CH_2=CHSO_2-C-SO_2CH=CH_2 \\ \| \\ CONH_2 \end{array}$ | Compound H-7 |
| $\begin{array}{c} CH_2CONH_2 \\ \| \\ CH_2=CHSO_2-C-SO_2CH=CH_2 \\ \| \\ CH_2CONH_2 \end{array}$ | Compound H-8 |
| $\begin{array}{c} CONH_2 \\ \| \\ CH_2=CHSO_2-C-SO_2CH=CH_2 \\ \| \\ CH_2CONH_2 \end{array}$ | Compound H-9 |
| $\begin{array}{c} CONHCH_3 \\ \| \\ CH_2=CHSO_2-C-SO_2CH=CH_2 \\ \| \\ CH_2CONH_2 \end{array}$ | Compound H-10 |
| $\begin{array}{c} CONH_2 \\ \| \\ CH_2=CHSO_2-C-SO_2CH=CH_2 \\ \| \\ CH_3 \end{array}$ | Compound H-11 |
| $\begin{array}{c} CONH_2 \\ \| \\ CH_2=CHSO_2-C-SO_2CH=CH_2 \\ \| \\ CH_2CO_2H \end{array}$ | Compound H-12 |

Preparation of the novel compounds of this invention is illustrated in the following examples.

Synthesis Example 1

(1) Synthesis of methyl 3-bis(2-hydroxyethylthio)propionate (1a)

A mixture of methyl propiolate (5.00 mL; 51.9 mmol) and mecaptoethanol (10.20 mL; 145.4 mmol) was heated to 100° C.. After 13.5 hours, 0.20 mL of DBU (1,8-diazabicyclo[5.4.0]undec-7-ene) was added and the temperature was increased to 115°-120° C. After 4 hours, the mixture was allowed to cool to room temperature and the remaining mercaptoethanol was removed under high vacuum with warming (40°-50° C.) to give 12.450 g (100%) of 1a.

$^1$H NMR (CDCl$_3$, δ): 4.41 (t, J=8 Hz, 1H), 3.84 (t,J=6 Hz, 4H), 3.75 (s, 3H), 2.79-2.99 (m, 4H), 2.10 (bs, 2H).

(2) Synthesis of methyl 3-bis (2-chloroethylthio) propionate (1b)

To a stirred solution of la (3.100 g; 12.90 mmol) and triphenylphosphine (8.460 g; 32.25 mmol) in 60 mL of THF under nitrogen at room temperature was added hexachloroacetone (4.17 mL; 27.5 mmol). After the addition, the mixture was stirred for 45 minutes and then concentrated under vacuum. The residue was extracted with 100 mL of 4/1 ethyl acetate/hexanes and the extract was concentrated under vacuum to give a brown oily semisolid. Flash chromotography on silica gel (eluent: ⅔ ethyl acetate/hexanes gave 3.988 g (112%) of brown oil. Volatile impurities were removed under high vacuum for 48 hours to give 3.458 g (100%) of 1b as a dark brown oil.

$^1$H NMR (CDCl$_3$, δ): 4.36 (t, J=7.5 HZ, 1H), 3.75 (s,3H), 3.70 (t, J=8 Hz, 4H), 2.93-3.11 (m, 4H), 2.83 (d, J=7.5 Hz, 2H).

(3) Synthesis of 3-bis (2-chloroethylthio)propionamide (1c)

To a stirred suspension of ammonium chloride (2.616 g; 0.049 mmol) in 50 mL of dry benzene under nitrogen at room temperature was added trimethylaluminum solution (Aldrich, 24.50 mL of 2.0 M solution in toluene). When gas evolution ceased (30 minutes) a solution of the ester 1b (4.500 g; 0.016 mmol in 15 mL of dry benzene) was added and then the mixture was warmed to 50° C. After 19 hours, the mixture was allowed to cool to room temperature and was then quenched by careful dropwise addition of 60 mL of 1.0 N HCl. The mixture was extracted several times with ethyl acetate and the combined extracts were dried (MgSO$_4$) and concentrated under vacuum. Flash chromatography on silica gel (eluent: 9/1 ethyl acetate/hexanes) gave 2.370 g (56%) of 1c, mp 56°-68° C.

¹H NMR (CDCl₃, δ): 5.63 (bm, 2H), 4.37 (t, J=7 Hz, 1H), 3.68 (m, 4H), 2.90-3.12 (m, 4H), 2.72 (d, J=7 Hz, 2H).

(4) Synthesis of 3-bis(2-chloroethylsulfonyl)propionamide (2b)

To a stirred solution of the amide 1c (3.000 g; 11.45 mmol) in 150 mL of CH₂Cl₂ at room temperature was added acetic acid (6.55 mL; 114.5 mmol) followed by hydrogen peroxide (7.80 mL of 50% w/w solution). After 45 h, the solvent was carefully removed under vacuum. The resulting residue was recrystallized from water and dried under vacuum over P₂O₅ to give 790 mg (21%) of 2b as a fine white powder, mp 135°-138° C.

(5) Synthesis of 3-bis (vinylsulfonyl)propionamide (3b)

To a stirred solution of 2b (1.015 g; 3.11 mmol) in 35 mL of dry THF under N₂ at room temperature was added triethylamine (0.87 mL; 6.22 mmol). After 10 min, the mixture was quenched by addition of 3.0 mL of 1.0 N HCl solution and the solvent was removed under vacuum. The residue was extracted several times with ethyl acetate and the combined extracts were dried (MgSO₄) and concentrated under vacuum. Flash chromatography on silica gel (eluent: 9/1 ethyl acetate/hexanes) gave 545 mg (74%) of 3b, mp 144°-146° C.

¹H NMR (acetone-d₆, δ): 7.07 (dd, J=10, 16 Hz, 2H), 7.06 (bs, 1H) , 6.63 (bs, 1H) , 6.41-6.46 (dd, J=10, 16 Hz, 2H), 5.17 (t, J=6 Hz, 1H), 2.97 (d, J=6 Hz, 2H). Anal. Calcd for C₇H₁₁NO₅S₂: C, 33.19; H, 4.39; N, 5.53. Found: C, 33.16, H, 4.41; N, 5.25.

Synthesis Example 2

(1) Synthesis of N-methyl-3-bis(2-chloroethylthio)propionamide (1d)

To a stirred suspension of methylamine hydrochloride (3.08 g; 0.049 mmol) in 50 mL of dry benzene under nitrogen at room temperature was added trimethylaluminum solution (Aldrich, 24.50 mL of 2.0 M solution in Toluene). After gas evolution ceased (30 min) a solution of the ester 1b (4.500 g; 0.016 mmol in 15 mL of dry benzene) was added and the mixture was warmed to 50° C. After 48 h, the mixture was allowed to cool to room temperature and was then quenched by careful dropwise addition of 60 mL of 1.0 N HCl. The mixture was extracted several times with ethyl acetate and the combined extracts were dried (MgSO₄) and concentrated under vacuum. Flash chromatography on silica gel (eluent: 4/1 ethyl acetate/hexanes) gave 2.050 g (37%) of 1d.

¹H NMR (CDCl₃, δ) 5.75 (bs, 1H), 4.41 (t, J=7 Hz, 1H) 3.64-3.74 (m, 4H), 2.96-3.13 (m, 4H), 2.85 (d, J=5 Hz, 3H), 2.66 (d, J=6 Hz, 2H). Anal. Calcd for C₈H₁₅Cl₂NOS₂: C, 34.78; H, 5.48; N, 5.07. Found: C, 35.18; H, 5.57; N, 4.85.

(2) Synthesis of N-methyl-3-bis(2-chloroethylsulfonyl)propionamide (2c)

To a stirred solution of 1d (3.00 g; 10.83 mmol) in 150 mL of CH₂Cl₂ at room temperature was added acetic acid (6.20 mL; 108.3 mmol) followed by hydrogen peroxide (7.37 mL of 50% w/w solution). After 45 h, the solvent was carefully removed under vacuum. The resulting residue was recrystallized from water and dried under vacuum over P₂O₅ to give 1.403 g (38%) of 2c as a fine white powder, mp 141°-143° C.

¹NMR (acetone-d₆, δ): 7.41 (bs, 1H), 5.54 (t, J=6 Hz, 1H), 3.86-4.10 (m, 8H), 3.16 (d, J=6 Hz, 2H), 2.75 (d, J=4 Hz, 3H).

(3) Synthesis of N-methyl-3-bis(vinylsulfonyl)propionamide (3c)

To a stirred solution of 2c (1.339 g; 3.93 mmol) in 40 mL of dry THF under N₂ at room temperature was added triethylamine (1.10 mL; 7.86 mmol). After 10 min, the mixture was quenched with 3.0 mL of 1.0 N HCl and the solvent was removed under vacuum. The residue was extracted several times with ethyl acetate and the combined extracts were dried (MgSO₄) and concentrated under vacuum. The residue was subjected to flash chromatography on silica gel (eluent: 4/1 ethyl acetate/hexanes) to give 638 mg (61%) of 3c, mp 116°-119° C.

¹H NMR (CDCl₃, δ): 6.98-7.07 (dd, J=10, 17 Hz, 2H), 6.55 (d, J=17 Hz, 2H), 6.34 (d, J=10 Hz, 2H), 5.87 (bs, 1H), 5.17 (t, J=6, 1H), 2.96 (d, J=6 Hz, 2H), 2.86 (d, J=5, 3H) . Anal. Calcd for C₈H₁₃NO₅S₂: C, 35.94; H, 4.91; N, 5.24. Found: C, 35.51; H, 4.95; N, 5.06.

Synthesis Example 3

(1) Synthesis of methyl bis (2-hydroxyethylthio) acetate (4a)

To a stirred solution of sodium methoxide in methanol (generated by dropwise addition of 100 mL of dry methanol to sodium hydride (7.872 g; 0.328 mol) at 0° C.) at room temperature was added mercaptoethanol (21.04 mL; 0.30 mol). After 10 min, the solvent was removed under vacuum and acetonitrile (250 mL) followed by methyl dichloroacetate (13.46 mL; 0.130 mol) were added. The mixture was stirred vigorously for 48 h at room temperature. The resulting white suspension was filtered through a bed of celite and the filtrate was concentrated under vacuum to give 11.808 g of 4a as an oil, which was used without purification.

(2) Synthesis of methyl bis(2-chloroethylthio)acetate (4b)

To a stirred solution of unpurified 4a (11.808 g, from above) and triphenylphosphine (31.37 g; 0.12 mol) in 150 mL of dry THF at room temperature was added hexachloroacetone (16.64 mL; 0.109 mol). After the addition, the resulting dark brown mixture was stirred for 30 min and then concentrated under vacuum. The residue was extracted with cold 1:4 ethyl acetate/hexanes and the extract was concentrated under vacuum. Flash chromatography on silica gel (eluent: ¼ ethyl acetate/hexanes) gave 4.312 g (21%) of 4b.

¹H NMR (CDCl₃, δ): 4.52 (s, 1H), 3.81 (s, 3H), 3.69-3.77 (m, 4H) , 3.07-3.14 (m, 4H) .

(3) Synthesis of N-methyl-bis(2-chloroethylthio)acetamide (4c)

To a stirred suspension of methylamine hydrochloride (3.464 g; 0.051 mol) in 60 mL of dry benzene under nitrogen at room temperature was added trimethylaluminum (Aldrich, 25.65 mL of 2.0M solution in toluene). After gas evolution ceased (30 min) a solution of the ester 4b (4.500 g; 0.017 mol in 10 mL of dry benzene was added and the mixture was warmed to 50° C. After 21 h, the mixture was allowed to cool to room temperature and was then quenched by dropwise addition of 60 mL of 1.0 N HCl. The mixture was extracted several times with ethyl acetate and the combined extracts were dried (MgSO$_4$) and concentrated under vacuum. Flash chromatography on silica gel (eluent: ⅔ ethyl acetate/hexanes) gave 2.849 g (64%) of 4c, mp 82°–84° C.

$^1$H NMR (CDCl$_3$, δ): 6.51 (bs, 1H), 4.50 (s, 1H), 3.69–3.73 (m, 4H), 3.04–3.10 (m, 4H), 2.88 (d, J=5 Hz, 3H). Anal Calcd for C$_7$H$_{13}$Cl$_{12}$NOS$_2$: C, 32.06; H, 5.01; N, 5.34. Found: C, 31.83; H, 4.98; N, 5.03.

(4) Synthesis of
N-methyl-bis(2-chloroethylsulfony)acetamide (5)

To a stirred solution of 70 mL of 10% sulfuric acid was added a solution of compound 4c (2.000 g; 7.62 mmol) in 100 mL of chloroform over a period of 20 min. During this period, potassium permanganate (12.054 g; 76.2 mmol) was added in several small portions (exotherm). The temperature of the reaction mixture was carefully monitored, and periodic cooling (ice bath) was used to maintain a temperature of 20°–25° C. After 30 min, the mixture was cooled to 0° C. and, with additional periodic cooling (ice bath) to maintain a temperature of 20°–25° C., a 20% sodium bisulfite solution was added dropwise until the brown color of the mixture dissipated. The mixture was extracted several times with ethyl acetate and the combined extracts were dried (MgSO$_4$) and concentrated under vacuum. The residue was recrystallized from ethyl acetate/hexanes to give 1.015 g (41%) of 5, mp 173°–175° C.

$^1$H NMR (acetone-d$_6$, δ): 7.92 (bs, 1H), 5.73 (s, 1H), 4.01–5.15 (m, 8H), 2.84 (d, J=5 Hz, 3H) .

(5) Synthesis of N-methyl-bis (vinylsulfonyl) acetamide (6)

To a stirred solution of 5 (600 mg; 1.84 mmol) in 80 mL of THF at 0° C. was added triethylamine (3.08 mL; 22.07 mmol). The mixture was allowed to warm to room temperature to 50 min and was then quenched with the addition of 22 mL of 1 N HCl. The mixture was concentrated under vacuum to about ⅓ initial volume and was extracted several times with ethyl acetate and the extracts were dried and concentrated under vacuum. The residue was dissolved in 80 mL of THF, the mixture was cooled to 0° C., and triethylamine (0.77 mL; 5.52 mmol) was added. The mixture was allowed to warm to room temperature for 10 min and was then quenched with 6 mL of 1 N HCl. The mixture was extracted several times with ethyl acetate and the combined extracts were dried and concentrated under vacuum. The resulting crude residue was recrystallized from ethyl acetate/hexanes to give 220 mg (47%) of 6, mp 143°–147° C.

$^1$H NMR (CDCl$_3$, δ): 6.94–7.03 (dd, J=16.5, 10 Hz, 2H), 6.71 (bs, 1H) , 6.59 (d, J=16.5 Hz, 2H), 6.39 (d, j=10 Hz, 2H), 5.04 (s, 1H), 2.97 (d, J=5 Hz, 3H). Anal. Calcd for C$_7$H$_{11}$NO$_5$S$_2$: C, 33.19; H, 4.39; N, 5.53. Found: C, 33.13; H, 4.36; N, 5.26.

The novel compounds of this invention are useful for hardening gelatin and in particular for hardening gelatin contained in one or more layers of a photographic light-sensitive element. The amount of the hardening agent to be used in the present invention can be selected appropriately depending on the intended use, and preferably ranges from 0.01 to 20% by weight, more preferably from 0.05 to 10% by weight and most preferably 0.1 to 5% by weight, based on the weight of dry gelatin.

The photographic elements of the present invention may be simple elements or multilayer, multicolor elements. Multicolor elements contain dye image-forming units sensitive to each of the three primary regions of the visible light spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprising at least one red-sensitive silver halide emulsion layer having associated therewith at least one cyan dye-forming coupler; a magenta image-forming unit comprising at least one green-sensitive silver halide emulsion layer having associated therewith at least one magenta dye-forming coupler; and a yellow dye image-forming unit comprising at least one blue-sensitive silver halide emulsion layer having associated therewith at least one yellow dye-forming coupler. The element may contain additional layers, such as filter layers, interlayers, overcoat layers, subbing layers, and the like.

The element may also contain a transparent magnetic recording layer such as a layer containing magnetic particles on the underside of a transparent support, as in U.S. Pat. Nos. 4,279,945 and 4,302,523 and Research Disclosure 34390 of November 1992.

Typically, the element will have a total thickness (excluding the support) of from about 5 to about 30 microns.

In the following discussion of suitable materials for use in the elements of this invention, reference will be made to *Research Disclosure*, December 1978, Item 17643, and *Research Disclosure*, December 1989, Item No. 308119, both published by Kenneth Mason Publications, Ltd., Dudley Annex, 12a North Street, Emsworth, Hampshire PO10 7DQ, ENGLAND, the disclosures of which are incorporated herein by reference. These publications will be identified hereafter by the term "Research Disclosure." A reference to a particular section in "Research Disclosure" corresponds to the appropriate section in each of the above-identified *Research Disclosures*. The elements of the invention can comprise emulsions and addenda described in these publications and publications referenced in these publications.

The silver halide emulsions employed in the elements of this invention can be comprised of silver bromide, silver chloride, silver iodide, silver bromochloride, silver iodochloride, silver iodobromide, silver iodobromochloride or mixtures thereof. The emulsions can include silver halide grains of any conventional shape or size. Specifically, the emulsions can include coarse, medium or fine silver halide grains. High aspect ratio tabular grain emulsions are specifically contemplated, such as those disclosed by Wilgus et al. U.S. Pat. Nos. 4,434,226, Daubendiek et al. 4,414,310, Wey 4,399,215, Solberg et al. 4,433,048, Mignot 4,386,156, Evans et al. 4,504,570, Maskasky 4,400,463, Wey et al. 4,414,306, Maskasky 4,435,501 and 4,643,966 and Daubendiek et al. 4,672,027 and 4,693,964, all of which are incorporated herein by reference. Also specifically contemplated are those silver iodobromide grains with a higher molar proportion of iodide in the core of the grain than in the periphery of the grain, such as those described in British Reference No. 1,027,146; Japanese Reference No. 54/48,521; U.S. Patent Nos. 4,379,837; 4,444,877; 4,665,012; 4,686,178; 4,565,778; 4,728,602; 4,668,614 and 4,636,461; and in European Reference No 264,954, all which are incorporated herein by reference. The silver halide emulsions can be either monodisperse or polydisperse as precipitated. The grain size distribution of the emulsions can be controlled by silver halide grain separation techniques or by blending silver halide emulsions of differing grain sizes.

Sensitizing compounds, such as compounds of copper, thallium, lead, bismuth, cadmium and Group VIII noble metals, can be present during precipitation of the silver halide emulsion.

The emulsions can be surface-sensitive emulsions, i.e., emulsions that form latent images primarily on the surface of the silver halide grains; or internal latent image-forming emulsions, i.e., emulsions that form latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

The silver halide emulsions can be surface-sensitized, and noble metal (e.g., gold), middle chalcogen (e.g., sulfur, selenium, or tellurium) and reduction sensitizers, employed individually or in combination, are specifically contemplated. Typical chemical sensitizers are listed in Research Disclosure, Item 308119, cited above, Section III.

The silver halide emulsions can be spectrally sensitized with dyes from a variety of classes, including the polymethine dye class, which includes the cyanines, merocyanines, complex cyanines and merocyanines (i.e., tri-, tetra-, and polynuclear cyanines and merocyanines), oxonols, hemioxonols, stryryls, merostyryls, and streptocyanines. Illustrative spectral sensitizing dyes are disclosed in Research Disclosure, Item 308119, cited above, Section IV.

Suitable vehicles for the emulsion layer and other layers of elements of this invention are described in Research Disclosure, Item 308119, Section IX and the publications cited therein.

The elements of this invention can include couplers, such as those described in Research Disclosure, Section VII, paragraphs D, E, F, and G and the publications cited therein. The couplers can be incorporated as described in Research Disclosure, Section VII, paragraph C, and the publications cited therein.

The photographic elements of this invention can contain brighteners (Research Disclosure, Section V), antifoggants and stabilizers (Research Disclosure, Section VI), antistain agents and image dye stabilizers (Research Disclosure, Section VII, paragraphs I and J), light absorbing and scattering materials (Research Disclosure, Section VIII), hardeners (Research Disclosure, Section X), coating aids (Research Disclosure, Section XI), plasticizers and lubricants (Research Disclosure, Section XII), antistatic agents (Research Disclosure, Section XIII), matting agents (Research Disclosure, Section XII and XVI) and development modifiers (Research Disclosure, Section XXI.

The photographic elements can be coated on a variety of supports as described in Research Disclosure, Section XVII and the references described therein.

The photographic elements of the invention can be exposed to actinic radiation, typically in the visible region of the spectrum, to form a latent image as described in Research Disclosure, Section XVIII, and then processed to form a visible dye image as described in Research Disclosure, Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylenediamines. Especially preferred are 4-amino-3-methyl-N,N-diethylaniline hydrochloride, 4-amino-3-methyl-N-ethyl-N-($\beta$-methanesulfonamidoethyl)-aniline sulfate hydrate, 4-amino-3-methyl-N-ethyl-N-($\beta$-hydroxyethyl)-aniline sulfate, 4-amino-3-($\beta$-methanesulfonamidoethyl)-N,N-diethylaniline hydrochloride, and 4-amino-N-ethyl-N-($\beta$-methoxyethyl)-m-toluidine di-p-toluenesulfonic acid. With negative-working silver halide, the processing step described above provides a negative image. The described elements are preferably processed in the known C-41 color process as described in, for example, the British Journal of Photography Annual, 1988, pages 196-198. To provide a positive (or reversal) image, the color development step can be preceded by development with a non-chromogenic developing agent to develop exposed silver halide, but not from dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver or silver halide, washing, and drying.

The invention is further described in the following examples.

Coating Examples 1–7

Comparative compounds as well as compounds of the invention were applied as an aqueous overcoat at a level of 0.1 millimole of compound per gram of gelatin to an unhardened coating of 900 mg/ft² gelatin on an Estar film support, resulting in Coating Samples 1 through 7 (Table 2). The vertical swell of the coatings was measured in distilled water at 20° C. at various times while the coatings aged in air of 25° C., RH. The change in x-swell from 0.1 days to 10 days was calculated from a linear regression analysis of x-swell versus log (coating age). Those results are shown in Table 2.

TABLE 2

| Coating Sample | Compound | 0.1 to 10 days afterhardening[a] |
|---|---|---|
| 1[c] | CH-1 | 1.43 |
| 2[c] | CH-2 | 2.53 |
| 3[c] | CH-3 | 2.10 |
| 4[i] | H-2 | 2.47 |
| 5[i] | H-3 | 2.49 |
| 6[i] | H-4 | 1.43 |
| 7[i] | H-5 | 1.55 |

[a]Estimated change in x-swell from 0.1 to 10 days of coating age
[c]Comparison example
[i]Example of the present invention Comparison hardeners included in Table 2 are as follows.

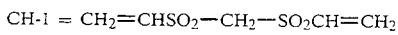

$CH\text{-}1 = CH_2\!\!=\!\!CHSO_2-CH_2-SO_2CH\!\!=\!\!CH_2$

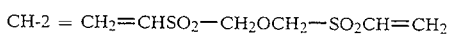

$CH\text{-}2 = CH_2\!\!=\!\!CHSO_2-CH_2OCH_2-SO_2CH\!\!=\!\!CH_2$

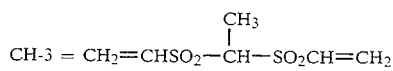

$$CH\text{-}3 = CH_2\!\!=\!\!CHSO_2-\underset{\underset{CH_3}{|}}{CH}-SO_2CH\!\!=\!\!CH_2$$

It is apparent from the results in Table 2 that the compounds of this invention are useful as gelatin hardeners. None of the coatings that were overcoated with the compounds of this invention were tacky. None of the compounds of this invention release by-products upon reaction with gelatin. None of the compounds of this invention are hygroscopic.

This invention has been described with particular reference to preferred embodiments thereof. A skilled practitioner familiar with the above detailed description can make many substitutions and additions without department from the scope and the spirit of the attached claims. For example, it will be apparent to one of skill in the art that the hardeners of this invention can be used to harden (i.e., crosslink) other polymers containing reactive amino groups.

What is claimed is:

1. Gelatin hardened with a compound represented by the formula:

$$CH_2=CHSO_2-\underset{\underset{\displaystyle }{|}}{CH}-SO_2CH=CH_2.$$
$$\overset{CH_2CONH_2}{|}$$

2. Gelatin hardened with a compound represented by the formula:

$$CH_2=CHSO_2-\underset{\underset{\displaystyle }{|}}{CH}-SO_2CH=CH_2.$$
$$\overset{CH_2CONHCH_3}{|}$$

3. Gelatin hardened with a compound represented by the formula:

$$CH_2=CHSO_2-\underset{\underset{\displaystyle }{|}}{CH}-SO_2CH=CH_2.$$
$$\overset{CH_2CON(CH_3)_2}{|}$$

4. A method for hardening gelatin comprising reacting gelatin with a compound of the formula:

$$CH_2=CHSO_2-\underset{\underset{\displaystyle R_3}{|}}{\overset{\overset{\displaystyle (CH_2)_nCONR_1R_2}{|}}{C}}-SO_2CH=CH_2$$

wherein $R_1$ and $R_2$ represent hydrogen or alkyl, $R_3$ represents hydrogen, alkyl, substituted alkyl or $COR_1R_2$ and n is 1 to 6.

* * * * *